United States Patent
Slupska et al.

(10) Patent No.: US 11,441,117 B2
(45) Date of Patent: Sep. 13, 2022

(54) FERMENTATION EFFICIENCY USING YEAST CONTAINING PRIONS

(71) Applicant: POET Research, Inc., Sioux Falls, SD (US)

(72) Inventors: Malgorzata Maria Slupska, Sioux Falls, SD (US); Stephen M. Lewis, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 189 days.

(21) Appl. No.: 16/653,955

(22) Filed: Oct. 15, 2019

(65) Prior Publication Data

US 2020/0115672 A1 Apr. 16, 2020

Related U.S. Application Data

(60) Provisional application No. 62/746,355, filed on Oct. 16, 2018.

(51) Int. Cl.
| | |
|---|---|
| *C12N 9/16* | (2006.01) |
| *C12N 1/20* | (2006.01) |
| *C12N 1/18* | (2006.01) |
| *C12N 15/81* | (2006.01) |
| *C07K 14/395* | (2006.01) |

(52) U.S. Cl.
CPC .............. *C12N 1/18* (2013.01); *C07K 14/395* (2013.01); *C12N 15/81* (2013.01)

(58) Field of Classification Search
CPC C07K 14/395; C12P 7/12; C12N 1/24; C12N 15/81
See application file for complete search history.

(56) References Cited

U.S. PATENT DOCUMENTS

| | | | | |
|---|---|---|---|---|
| 8,679,803 B2* | 3/2014 | Czechowski | ............ | C12N 1/38 435/161 |
| 10,023,837 B2* | 7/2018 | Goebl | .................... | C12N 15/01 |
| 10,889,836 B2* | 1/2021 | Yazdi | ................... | C12N 9/2417 |

OTHER PUBLICATIONS

Brown et al. (2009) "A heritable switch in carbon source utilization driven by an unusual yeast prion" Genes. Dev. 23:2320-2332.
Farwick et al. (2014) "Engineering of yeast hexose transporters to transport D-xylose without inhibition by D-glucose" PNAS 111:5159-5164.
Galdieri et al. (2010) "Transcriptional Regulation in Yeast during Diauxic Shift and Stationary Phase" OMICS 14:629-638.
Görke et al. (2008) "Carbon catabolite repression in bacteria: many ways to make the most out of nutrients" Nature Reviews 6:613-624.
Jarosz et al. (2014) "An Evolutionarily Conserved Prion-like Element Converts Wild Fungi from Metabolic Specialists to Generalists" Cell 158:1072-1082.
Jarosz et al. (2014) "Cross-Kingdom Chemical Communication Drives a Heritable, Mutually Beneficial Prion-Based Transformation of Metabolism" Cell 158:1083-1093.
Jeffries et al. (2004) "Metabolic engineering for improved fermentation of pentoses by yeasts" App. Microbiol. Biotech 63:495-509.
Johnston (1999) "Feasting, fasting and fermenting: glucose sensing in yeast and other cells" Trends Genet. 15:29-33.
Mitchelitsch et al. (2000) "A census of glutamineyasparagine-rich regions: Implications for their conserved function and the prediction of novel prions" PNAS 97(22):11910-11915.
Sanchez et al. (2010) "Improved xylose and arabinose utilization by an industrial recombinant *Saccharomyces cerevisiae* strain using evolutionary engineering" Biotechnology for Biofuels. 3:13.
Walker et al. (2016) "Impact of the [GAR+] Prion on Fermentation and Bacterial Community Composition with *Saccharomyces cerevisiae* UCD932" A. J. Enol. Vitc. 67:296-307.
Zampar et al. (2013) "Temporal system-level organization of the switch from glycolytic to gluconeogenic operation in yeast" Mol. Syst. Biol. 9:65.

* cited by examiner

*Primary Examiner* — Tekchand Saidha
(74) *Attorney, Agent, or Firm* — FisherBroyles, LLP; Cara L. Crowley-Weber; Cary Reeves

(57) ABSTRACT

Genetically modified microorganisms useful in fermentation and methods of using such microorganisms are provided. Such microorganisms contain a [GAR+] prion or are modified to contain a [GAR+] prion. Exemplary microorganisms include yeast such as *S. cerevisiae*. The microorganisms can be further modified to convert xylose and/or arabinose. Methods of fermentation using such microorganisms exhibit improved fermentation efficiency and improved microorganism viability.

20 Claims, No Drawings

FERMENTATION EFFICIENCY USING YEAST CONTAINING PRIONS

CROSS-REFERENCE TO RELATED APPLICATIONS

This application claims priority under 35 U.S.C. 119(e) to U.S. Provisional Patent Application Ser. No. 62/746,355, filed Oct. 16, 2018, the disclosure of which is hereby incorporated by reference in its entirety.

TECHNICAL FIELD

Yeast conversion of non-glucose C5/C6 sugars can be improved by eliminating sequential (two or more) growth stages of organisms grown on mixed carbon sources, thereby improving fermentation kinetics.

BACKGROUND

*Saccharomyces cerevisiae* are specialized organisms that ferment glucose to ethanol. When glucose is present in the environment, an ancient biological circuit in yeast turns off pathways for utilization of other carbon sources (Johanston, 1999). This mechanism of "glucose associated repression" (GAR) is known in many organisms but is particularly stringent in yeast (Gorke and Stulke, 2008). This characteristic enables fast growth and out-competition of other organisms in an environment rich in glucose.

When yeast switch from utilizing glucose to another carbon source, the microorganisms enter a pronounced lag phase known as diauxic shift. The pause in growth occurs because a new transcriptional program is initiated (Galdieri et al., 2010; Zampar et al., 2013) and enzymes are produced for metabolism of the secondary carbon source. In cellulosic feedstock where sugars like xylose and arabinose are in abundance, glucose repression and diauxic shift result in inefficient sugar utilization and lower ethanol yields.

Improved xylose utilization is typically achieved by targeted metabolic engineering to increase transcription or activity of genes involved in xylose metabolism (Jefferies and Jin, 2004), or by modification of yeast hexose transporters Hxt7 and Gal2 to yield glucose insensitive xylose transporters (Farwick et al., 2014). Another approach is the evolution of genetically engineered yeast for better xylose utilization (Sanchez et al., 2010).

Alternative approaches to improved cellulosic conversion in fermentation are needed.

SUMMARY

The [GAR+] prion involves a complex between a small fraction of the cellular complement of Pma1, the major plasma membrane proton pump, and Std1, a much lower-abundance protein that participates in glucose signaling (minor pump). The [GAR+] prion may be present in some yeasts and inactivates glucose-associated repression so that the yeast may non-preferentially utilize a mixture of sugars. Provided herein are yeast useful in fermentations of multi-sugar feedstocks. In some aspects, the yeast is *Saccharomyces cerevisiae* comprising the [GAR+] prion, such as, for example, the *Saccharomyces cerevisiae* strain UCD932. In some aspects, the yeast non-preferentially ferments all C6 (six-carbon) sugars, such as glucose, mannose and/or galactose. In some aspects, the yeast is genetically modified to express saccharification enzymes such as glucoamylase, alphaamylase, and/or other desirable enzymes. In some aspects, the yeast is genetically modified to utilize C5 (five-carbon) sugars such as xylose and/or arabinose. In some aspects, the yeast is genetically modified to express saccharification enzymes such as cellulases, beta-glucosidases, xylanases, and LPMOs, and/or other useful enzymes. In some aspects, the yeast utilizes two or more sugars simultaneously during the exponential phase of fermentation.

Such yeasts are useful in methods of fermentation, and fermentation performance is improved relative to [gar−] yeast. As such, provided herein are methods of using [GAR+] yeast in fermentation. In an example, a method comprises inoculating a feedstock and fermenting the feedstock with a [GAR+] yeast.

In some aspects, the use of a [GAR+] yeast in fermentation improves efficiency of conversion of non-glucose C6 sugars. In some aspects, the use of a [GAR+] yeast in fermentation improves efficiency of conversion of mannose and/or galactose.

In some aspects, the use of a [GAR+] yeast genetically modified to convert C5 sugars in fermentation improves efficiency of conversion of xylose and/or arabinose in a mixed C6/C5 carbon source.

The methods provided herein can improve fermentation efficiency by increasing ethanol yield, increasing fermentation rate, and/or by improving yeast viability. In some aspects, two or more sugars are converted during an exponential phase of fermentation.

In some aspects, the use of a [GAR+] yeast permits simultaneous conversion of multiple C6 sugars including glucose, mannose, and/or galactose. Provided herein is a method of improving fermentation efficiency of a waste stream substrate, such as waste streams from the pulp and paper industry. For example, red liquor from the pulp and paper industry contains multiple C6 sugars. For example, a method comprises inoculating a red liquor waste feedstock with *Saccharomyces cerevisiae* containing the [GAR+] prion, such as the *Saccharomyces cerevisiae* strain UCD932, and fermenting the feedstock. In some aspects, the conversion of mannose and galactose is improved. Other waste stream substrates are contemplated as useful according to the embodiments provided herein.

Also provided are methods for modifying a [GAR+] yeast to enable the yeast to convert xylose and/or arabinose. [GAR+] yeast can be genetically modified to add C5 sugar conversion pathways. Such [GAR+] yeast can simultaneously convert the C5 and C6 sugars resulting from hydrolyzing glucan and xylan in, e.g., lignocellulosic feedstocks, e.g. wood, grasses, crop residue, e.g., cereal straw, corn stover (cobs, leaves, stalks), etc.

It is further contemplated that any of the yeasts provided herein can be genetically engineered to express saccharification enzymes. Additional genetic modifications can be made to confer other desirable traits into the [GAR+] yeast.

Also provided are methods for modifying a yeast to contain a [GAR+] prion.

Other objects and advantages will become apparent from a review of the ensuing detailed description.

DESCRIPTION

Before the present compositions and methods are described, it is to be understood that this invention is not limited to particular compositions, methods, and experimental conditions described, as such may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

In a typical ethanol production plant, corn, or other suitable feedstock is ground for fermentation. The entire corn kernel can be ground for fermentation, or the corn kernel may be fractionated into its component parts, and only the starchy endosperm ground for use in fermentation. Any suitable feedstock, subjected to virtually any suitable pretreatment, may be used in the methods provided herein.

The ground corn or other feedstock may be combined with water to form a slurry, and the pH of the slurry mixture may be adjusted as needed. A yeast such as *S. cerevisiae* is added to the fermenter. The amount of yeast starter employed is selected to effectively produce a commercially significant quantity of ethanol in a suitable time, e.g., less than 75 hours or less than 88 hours.

Yeast can be added to the fermentation by any of a variety of methods known for adding yeast to fermentation processes. For example, yeast can be added as active dry yeast, crème yeast, or other forms. Yeast can be added directly to a fermentation vessel or it may be propagated and/or conditioned prior to adding to a fermentation vessel. In an embodiment, yeast is added as a single inoculation. In an embodiment, yeast is added to the fermentation during the fermenter fill at a rate of 5 to 100 pounds of active dry yeast (ADY) per 100,000 gallons of fermentation mash. In an embodiment, the yeast can be acclimated or conditioned by incubating about 5 to 50 pounds of ADY per 10,000 gallon volume of fermenter volume in a prefermenter or propagation tank. Incubation can be from 8 to 16 hours during the propagation stage. The prefermenter used to inoculate the main fermenter can be from 1 to 10% by volume capacity of the main fermenter, for example, from 2.5 to 5% by volume capacity relative to the main fermenter. In an embodiment, aeration is used during at least a portion of fermentation fill and/or during propagation in a prefermenter to encourage yeast growth.

Other desired nutrients can be added to the fermenter, including certain enzymes which produce monomeric sugars from polymeric sugars (e.g. glucose from starch) in the fermentable solids as in simultaneous saccharification and fermentation (SSF). These enzymes can be commercially sourced, may be present in the feedstock (genetically modified corn, for example), or may be expressed by the yeast. Exemplary enzymes include glucoamylase and alpha-amylase. Alternatively, saccharification can be performed separate from fermentation.

The slurry can be held at specified temperatures to facilitate the production of ethanol for a determined period of time. Fermenting can include contacting a mixture including sugars from the reduced feedstock (e.g., ground grain) with yeast under conditions suitable for growth of the yeast and production of ethanol. During fermentation, the yeast converts the glucose to ethanol and carbon dioxide. The rate of enzymatic production of glucose (saccharification) and the rate of the fermentation process may be established so that the level of glucose may be maintained in the system at a low steady state. After fermentation, further treatment and/or distillation is performed to recover the ethanol, oil, CO2, dried distiller's grains (DDGs), and/or other co-products.

Monomeric glucose is the predominant sugar metabolized by yeast, e.g. *Saccharomyces cerevisiae*, to produce ethanol. However, other sugars can be present in a feedstock, including for example, xylose and/or mannose.

Provided herein are methods of boosting conversion of non-glucose C5/C6 sugars and/or increasing fermentation kinetics by eliminating the sequential (two or more) growth stages of microorganisms grown on a mixture of carbon sources. In some embodiments, the microorganisms are yeast, such as *S. cerevisiae*.

Yeast prions are intracellular proteins capable of existing in at least two stable states. These prions act as heritable epigenetic "switches" that allow a portion of a cell population to adapt dynamically to environmental stress. A population of yeast undergoing stress will spontaneously induce these prion states allowing a subset of the population to sample new phenotypes and/or modes of metabolism. These prion states often mimic mutant phenotypes, serving a parallel purpose, but in a dynamic manner without the threat of permanently affecting the population genome or long-term fitness. Thus, prions promote phenotypic diversity in the absence of genetic mutations, thereby protecting the original genotype under variable and stressful environmental conditions.

Diauxie (i.e. the diauxic shift) is the typical growth phases of a microorganism as it metabolizes a mixture of two sugars: rather than metabolizing the two available sugars simultaneously, yeast consumes the two sugars sequentially resulting in two growth phases. Most commercial yeast exhibit a strong bias toward glucose such that when glucose is present the yeast cells turn off pathways (complexes of genes or operons encoding proteins) necessary for utilization of other sugars. When glucose levels drop, induction of the other pathways requires time and during the transition period yeast display slower ethanol production. An exemplary prion, the [GAR+] prion, inactivates glucose-associated repression in yeast. While not wishing to be held to theory, it is believed that yeast containing the [GAR+] prion can simultaneously metabolize multiple sugars, avoiding the delay needed for the metabolic switch from the preferred sugar, glucose, to the other sugars present in the feedstock, improving sugar metabolism and ethanol production.

[GAR+] strains are unexpectedly useful in cellulosic fermentations leading to enhanced kinetics in glucose/xylose or glucose/mannose fermentations, even when glucose is a significant or majority component of the feedstock. One of skill in the art would have reasonably expected that lactic acid bacteria overgrowth would limit the effectiveness of [GAR+] strains to utilize non-glucose carbon sources, leading to stuck and sluggish fermentations in glucose rich substrates. Walker et al. (2016, A. J. Enol. Vitc., 67: 296-307) proposed that yeast containing prions was a factor in sluggish fermentations, reducing ethanol production and glucose consumption. Others report reduced ethanol yield (Jarosz et al., 2014, Cell, 158: 1083-1093). However, it has been determined herein that in short commercial fermentations, the advantage of simultaneous sugar utilization benefits cellulosic fermentation.

*Saccharomyces cerevisiae* has strong glucose-associated repression (GAR), such that when glucose is present the yeast prioritize the fermentation of glucose and represses utilization of other carbon sources. Yeasts genetically modified to utilize C5 sugar (e.g. xylose) pathways can metabolize C5 sugars but do so slowly.

Provided herein are yeast strains containing the [GAR+] prion, such as *Saccharomyces cerevisiae* strain UCD932, that are further genetically engineered for use in commercial ethanol production. The UCS932 strain can spontaneously generate the [GAR+] phenotype. Such yeast strains can be genetically engineered to include a C5 sugar pathway to increase C5 sugar utilization as well as overall fermentation rate. By circumventing glucose-associate repression, the yeast will utilize the C5 sugars simultaneously with glucose. Also provided herein are yeast strains engineered to induce prions that that allow the cell to circumvent glucose repression of alternative carbon substrates.

[GAR+] yeast strains useful according to the embodiments provided herein have one or more of the following characteristics:
- can shift fermentation of a multiple sugar feedstock into the exponential phase making the fermentation faster and higher yielding;
- when genetically modified to contain C5 sugar metabolic pathway, can circumvent GAR and utilize the C5 sugars simultaneously with glucose;
- can increase non-glucose C6 sugar (e.g. mannose, galactose) utilization;
- can increase overall fermentation rate in feedstocks that contain significant amounts of non-glucose C6 sugars in addition to glucose (e.g. red liquor waste from pulp and paper processes); or
- can be used without C5 pathway in fermentations where feedstock contains predominantly C6 sugars (e.g. red liquor waste).

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

All C5 fermenting yeast tested utilized xylose less efficiently than glucose, frequently uptaking xylose only after glucose was depleted and/or leaving xylose or arabinose behind.

Red liquor waste feedstock from the pulp/paper industry is inoculated with *Saccharomyces cerevisiae* strain UCD932 containing the [GAR+] prion. Fermentation proceeds for 48-72 hours and increased ethanol production is found relative to prion free *Saccharomyces cerevisiae* fermentation of red liquor feedstock.

*Saccharomyces cerevisiae* strain UCD932 containing the [GAR+] prion is genetically modified to contain the C5 sugar metabolic pathway. When inoculated on lignocellulosic hydrolysate, the fermentation demonstrated increased C5/C6 carbon utilization in the exponential phase of fermentation and increased ethanol production.

*Saccharomyces cerevisiae* strain UCD932 containing the [GAR+] prion is genetically modified to express enzymes including cellulases, beta-glucosidases, xylanases, LPMOs, glucoamylase, alphaamylase, and/or phosphoketalase (any desirable enzymes). These yeast are used in simultaneous saccharification/fermentation of feedstock containing polymers comprised of different sugar monomers and demonstrate increased ethanol production relative to non-modified UCD932 yeast and commercially available *Saccharomyces cerevisiae*.

The invention claimed is:

1. A method of producing ethanol from a multi-sugar feedstock having a blend of 5-carbon sugars and 6-carbon sugars, the method comprising inoculating the multi-sugar feedstock with [GAR+] *Saccharomyces cerevisiae* strain, which contains a C5 sugar metabolic pathway to ferment xylose and/or arabinose, and fermenting the feedstock, wherein:
    the [GAR+] *Saccharomyces cerevisiae* strain utilizes 5-carbon and 6-carbon sugars simultaneously during fermentation of the multi-sugar feedstock and ethanol is produced from the feedstock.

2. The method of claim 1, wherein the [GAR+] *Saccharomyces cerevisiae* is UCD932.

3. The method of claim 1, wherein the feedstock is red liquor waste.

4. The method of claim 1 wherein the [GAR+] *Saccharomyces cerevisiae* strain is genetically modified to comprise the C5 sugar metabolic pathway.

5. The method of claim 4, wherein the [GAR+] *Saccharomyces cerevisiae* strain is further modified to express saccharification enzymes.

6. The method of claim 5, wherein the saccharification enzymes are selected from cellulases, beta-glucosidases, xylanases, and LPMOs.

7. The method of claim 4, wherein the 5-carbon sugar is xylose and the 6-carbon sugar is glucose and both are used simultaneously during fermentation.

8. The method of claim 1 wherein ethanol production is improved relative to fermentation using [GAR−] yeast.

9. The method of claim 1, wherein the [GAR+] *Saccharomyces cerevisiae* strain is modified to express at least one of cellulases, beta-glucosidases, xylanases, and LPMOs.

10. The method of claim 1, wherein the [GAR+] *Saccharomyces cerevisiae* strain is genetically modified to use xylose and/or arabinose.

11. The method of claim 1, wherein efficiency of conversion of non-glucose C6 sugars is improved relative to fermentation using [GAR−] yeast.

12. The method of claim 10, wherein the non-glucose C6 sugars are selected from mannose and galactose.

13. The method of claim 1, wherein the feedstock is lignocellulosic feedstock.

14. The method of claim 1, wherein the [GAR+] *Saccharomyces cerevisiae* strain is obtained by introducing a [GAR+] prion into a *Saccharomyces cerevisiae* strain.

15. The method of claim 1, wherein the [GAR+] *Saccharomyces cerevisiae* strain viability is improved relative to fermentation using [GAR−] yeast.

16. The method of claim 1, wherein fermentation using the [GAR+] *Saccharomyces cerevisiae* strain produces increased ethanol yield relative to fermentation using [GAR−] yeast.

17. The method of claim 1, wherein fermentation rate of the [GAR+] *Saccharomyces cerevisiae* strain is improved relative to fermentation using [GAR−] yeast.

18. The method of claim 1, wherein conversion of mannose and galactose is improved relative to fermentation using [GAR−] yeast.

19. A method of producing ethanol from a multi-sugar feedstock having a blend of 5-carbon sugars and 6-carbon sugars, the method comprising inoculating the multi-sugar feedstock with a [GAR+] *Saccharomyces cerevisiae* strain, which contains a C5 sugar metabolic pathway to ferment xylose and/or arabinose, and fermenting the feedstock, wherein:

the [GAR+] *Saccharomyces cerevisiae* strain utilizes the two or more sugars simultaneously during fermentation of the multi-sugar feedstock, ethanol is produced from the feedstock, and efficiency of conversion of non-glucose C6 sugars is improved relative to fermentation using [GAR−] yeast.

20. A method of producing ethanol from a multi-sugar feedstock having a blend of 5-carbon sugars and 6-carbon sugars, the method comprising inoculating the multi-sugar feedstock with a [GAR+] *Saccharomyces cerevisiae* strain, genetically modified to use xylose and/or arabinose, and fermenting the feedstock, wherein:

the [GAR+] *Saccharomyces cerevisiae* strain utilizes the two or more sugars simultaneously during fermentation of the multi-sugar feedstock and ethanol is produced from the feedstock.

\* \* \* \* \*